(12) United States Patent
Niu et al.

(10) Patent No.: US 6,538,731 B2
(45) Date of Patent: Mar. 25, 2003

(54) SYSTEM AND METHOD FOR CHARACTERIZING MACRO-GRATING TEST PATTERNS IN ADVANCED LITHOGRAPHY AND ETCH PROCESSES

(75) Inventors: Xinhui Niu, San Jose, CA (US); Nickhil Jakatdar, Fremont, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/068,311

(22) Filed: Feb. 5, 2002

(65) Prior Publication Data

US 2002/0131040 A1 Sep. 19, 2002

Related U.S. Application Data

(63) Continuation of application No. 09/770,857, filed on Jan. 26, 2001.

(51) Int. Cl.[7] ............................................. G01N 21/00
(52) U.S. Cl. ................................................... 356/237.5
(58) Field of Search .............................. 356/237.2, 354, 356/355, 356, 363, 384, 400, 401

(56) References Cited

U.S. PATENT DOCUMENTS

| 4,303,341 A | * | 12/1981 | Kleinknecht et al. | ....... 356/384 |
| 4,408,884 A | * | 10/1983 | Kleinknecht et al. | ....... 356/355 |
| 5,422,723 A | * | 6/1995 | Paranjpe et al. | ............ 356/355 |

* cited by examiner

Primary Examiner—Michael P. Stafira
(74) Attorney, Agent, or Firm—Morrison & Foerster LLP

(57) ABSTRACT

The invention teaches a method and system for an accurate profile characterization of test patterns that may be implemented for real time use in a fabrication line. One embodiment is a non-destructive method for acquiring file data of the test pattern lines through the use of spectrum data measured with an optical metrology device and a profile library. The profile data comprise critical dimensions of all the test pattern lines included in the set of parameters to create the profile library. The test pattern lines may be designed to evaluate the effectiveness of measures to correct optical proximity, micro-loading or other process effects.

20 Claims, 7 Drawing Sheets

<u>Trapezoidal with Top Rounding Profile
and Bottom Footing</u>

Footing bottom width ------------- w1
Trapezoidal bottom width--------- w2
% height bottom foot ----- (p1/h)*100
Total height ------------------------ h
% height of top rounding --- (p2/h)*100
Trapezoidal top width ------------- w3
Rounding top width --------------- w4

12   14   16

20   22   24   26   28

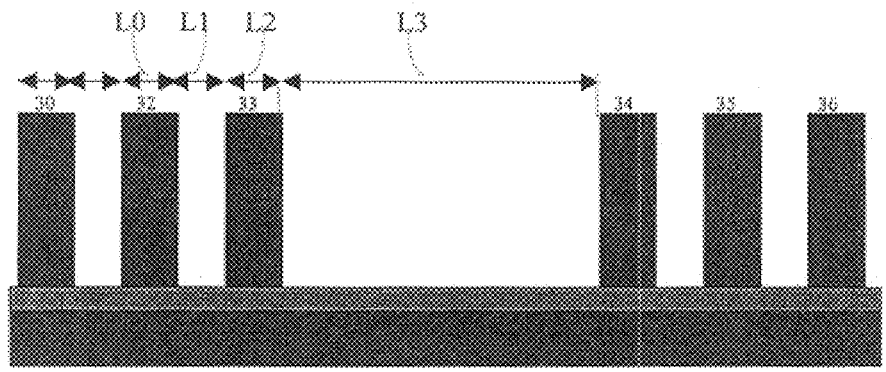
*FIGURE 5A*
|   | L0  | L1  | L2  | L3  |
|---|-----|-----|-----|-----|
| 1 | 150 | 150 | 150 | 250 |
| 2 | 150 | 160 | 140 | 250 |
| 3 | 150 | 140 | 160 | 250 |
*FIGURE 5B*
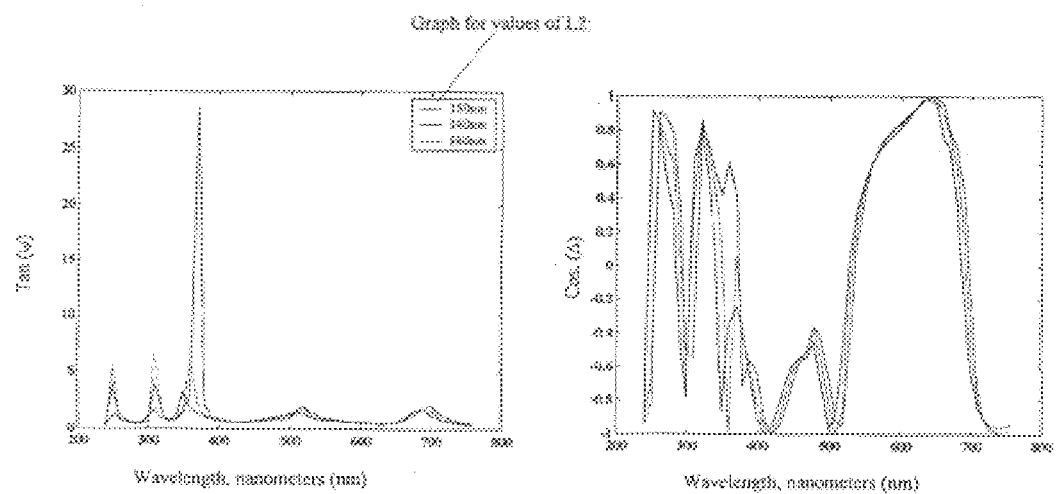
*FIGURE 5C*          *FIGURE 5D*

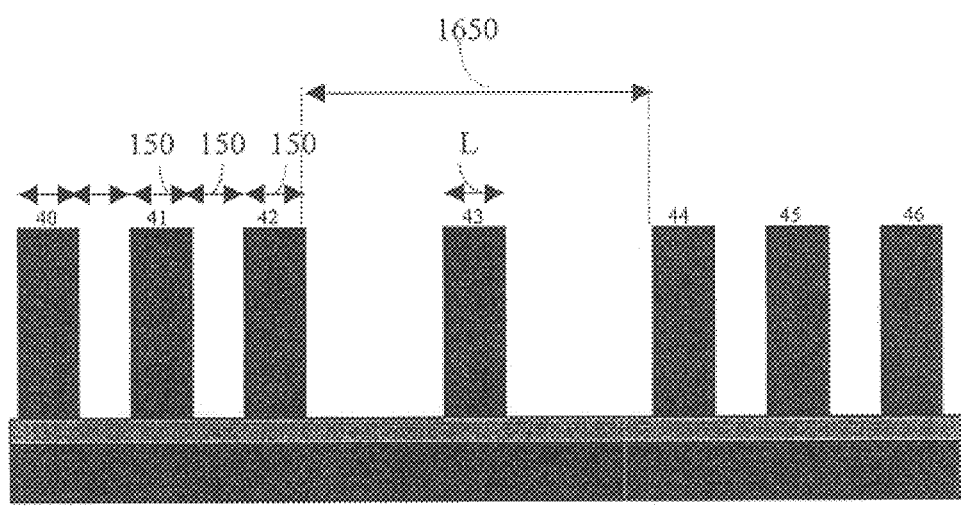
*FIGURE 6A*
|   | L (nm) |
|---|--------|
| 1 | 150    |
| 2 | 140    |
| 3 | 160    |
*FIGURE 6B*
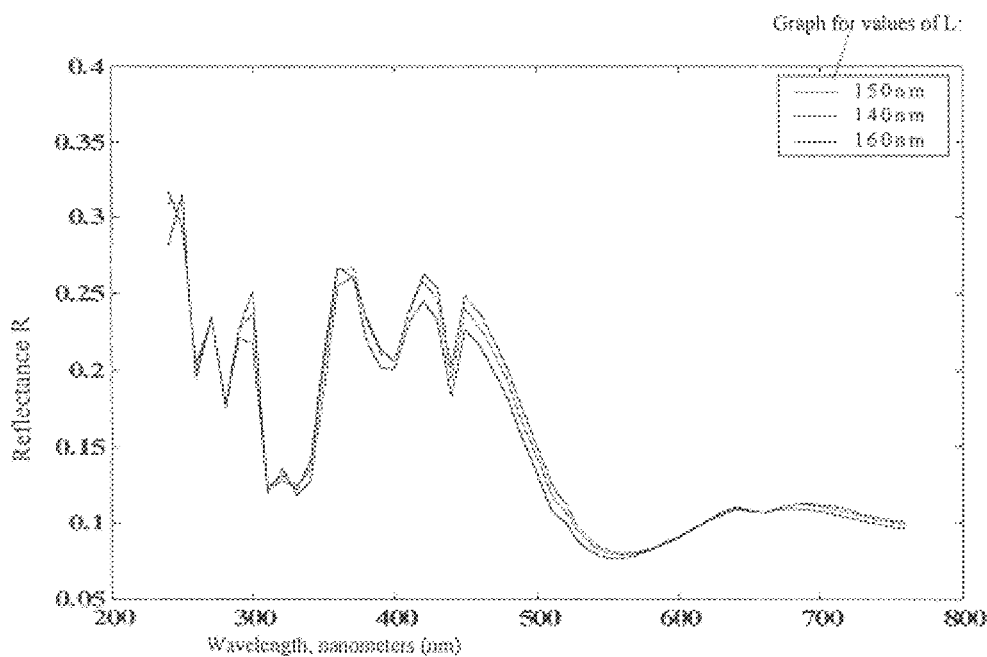
*FIGURE 6C*

SYSTEM AND METHOD FOR CHARACTERIZING MACRO-GRATING TEST PATTERNS IN ADVANCED LITHOGRAPHY AND ETCH PROCESSES

CROSS-REFERENCE TO RELATED APPLICATIONS

This application is a continuation of U.S. patent application Ser. No. 09/770,857 filed Jan. 26, 2001, and relates to co-pending U.S. patent application Ser. No. 09/727,530 entitled "System and Method for Real-Time Library Generation of Grating Profiles" by Jakatdar, et al., filed on Nov. 28, 2000, owned by the assignee of this application and incorporated herein by reference.

BACKGROUND INVENTION

1. Field of Invention

Invention relates to the field of process metrology in semiconductor manufacturing and more particularly to the pattern process characterization in advanced lithography and etch technology.

2. Description of Related Art

The semiconductor industry is faced with the increased need to make features with smaller critical dimensions. To address this need, lithography processes had to be extended with techniques such as optical proximity correction, phase shifting, scattering bars, and off-axis illumination, allowing the industry to extend the life of deep ultraviolet lithography beyond the sub-wavelength barrier.

In advanced lithography, the effect of optical proximity is pronounced and very significant. Optical proximity effect manifests itself in the features where the line ends become short or long depending on whether it is positive or negative resist is used, line widths increase or decrease based on local density patterns, corners are rounded instead of being at right angles. Some of the factors causing the optical proximity effect are optical factors such as the interference of light beams transmitted through adjacent patterns, variation in the resist processes influenced by the quality of the resist, bake temperature and length of wafer baking, and resist development time, reflection from the substrate, and irregularities of the substrate. Optical proximity correction (OPC) is the set of corrective measures used in lithography to compensate for the presence or absence of adjacent features. For example, for structure lines that become shorter and rounded, OPC measures may include lengthening the line and or using enlargements at the ends such as hammerheads and serifs. Alternatively, different parts of the pattern may be widened or narrowed to compensate for the projected optical proximity effect.

Micro loading effect is caused by the etching rate varying in a chip or wafer depending on the density of the pattern components. An area or segment of a pattern may be over-etched or under-etched based on number and type of nearby pattern components. Dummy patterns are used to compensate for the micro loading effect.

Phase shift mask is an advanced lithography process of shifting the intensity profile of the light for the purpose of controlling the focus settings so as to create an asymmetrical displacement of the photoresist pattern. The mask may employ multiple degrees of phase shifting across the mask depending on the pattern to be formed. The type of resist, the difference in the multiple phases of the light on each side of the light shielding pattern, the focus and length of light exposure may all be controlled collectively to provide the desired patterning results.

Test patterns are used to characterize optical proximity, micro loading, and other process effects. For example, the five-finger-bar pattern is commonly used to determine the process effect and corrective effect of a pattern design. Whether it is the use of OPC measures, dummy patterns to compensate for the micro loading effect, or the use of phase shift masks, there is a need for metrology methods to get a more two-dimensional or three-dimensional profile of the grating features of the test pattern in order to evaluate the effect of these corrective measures. Although there are numerous non-destructive techniques for linewidth measurements, such as the scanning electron microscope (SEM) and optical microscope, none of these methods can provide complete profile information. Cross-sectional profile metrology tools, such as the atomic force microscope (AFM) and the transmission electron microscope that provide profile information are either too slow and or destructive; thus, these metrology devices are not implemented for in line/in situ applications.

Two optical metrology equipment setups may be used in optical profile metrology to measure test patterns in a non-destructive manner: those of spectroscopic reflectometry and spectroscopic ellipsometry. In spectroscopic reflectometry, the reflected light intensities are measured in a broadband wavelength range. In most setups, nonpolarized light is used at normal incidence. The biggest advantage of spectroscopic reflectometry is its simplicity and low cost.

In reflectometry, only light intensities are measured. $R=|r|^2$ is the relation between the reflectance R and the complex reflection coefficient r.

In spectroscopic ellipsometry, the component waves of the incident light, which are linearly polarized with the electric field vibrating parallel (p or TM) or perpendicular (s or TE) to the plane of incidence, behave differently upon reflection. The component waves experience different amplitude attenuations and different absolute phase shifts upon reflection; hence, the state of polarization is changed. Ellipsometry refers to the measurement of the state of polarization before and after reflection for the purpose of studying the properties of the reflecting boundary. The measurement is usually expressed as:

$$\rho = \tan\Psi\exp(j\Delta) = \frac{r_p}{r_s}$$

where $r_p$ and $r_s$ are the complex reflection coefficient for TM and TE waves. Ellipsometry derives its sensitivity from the fact that the polarization-altering properties of the reflecting boundary are modified significantly even when ultra-thin films are present. Consequently, ellipsometry has become a major means of characterizing thin films.

The advantage of ellipsometry over reflectometry is its accuracy. First, ellipsometry measures the polarization state of light by looking at the ratio of values rather than the absolute intensity of the reflected light. Second, ellipsometry can gather the phase information in addition to reflectivity information. Phase information provides more sensitivity to the thin-film variation. Regardless of the technique used, there is a need for a non-destructive, high throughput accurate profile extraction tool for test patterns that can implemented real-time in a fabrication line.

SUMMARY OF INVENTION

Invention resides in a method and system for an accurate profile characterization of test patterns that can be implemented for real-time use in a fabrication line.

One embodiment of the present invention is a nondestructive method for acquiring the profile data of test pattern lines in a macro-grating test pattern, the method comprising fabricating a set of test patterns in a wafer, obtaining spectrum data from the set of test patterns using an optical metrology device, and accessing the profile data associated with the closest matching calculated spectrum data in a macro-grating profile library. The set of test patterns in the macro-grating test pattern comprises a number of clustered test pattern lines and a number of isolated test pattern lines. The set of test patterns in the wafer may be designed to evaluate the optical proximity, micro-loading, and other process effects.

In one embodiment, the optical metrology device comprises an ellipsometer or a reflectometer. Some applications of the present invention include obtaining of the spectrum data and accessing the profile data in real-time at the fabrication site. The profile data comprises detailed geometric information of each sub-feature of the macro-grating, such as width of test pattern lines, distances between test pattern lines, and or height of the features in the macro-grating test pattern.

The present invention also includes a system for acquiring the profile data of test pattern lines of a macro-grating test pattern comprising a macro-grating profile library generator for generating a macro-grating profile library comprising profile data and calculated spectrum data, an optical metrology device for measuring spectrum data from the macro-grating test pattern, and a profiler application server. The profiler application server compares the calculated spectrum data to the measured spectrum data from the optical metrology device, obtains the closest matching calculated spectrum data in a macro-grating profile library instance compared to the measured spectrum data, and accesses the associated profile data in the macro-grating profile library instance.

BRIEF DESCRIPTION OF DRAWINGS

FIG. 5A is a cross-sectional view of a macro-grating test pattern showing a configuration of three-line test pattern, a space, followed by another three-line test pattern.

FIG. 5B is a table of values of the variables used in a simulation of the reflected spectra from the test pattern in FIG. 5A.

FIGS. 5C and 5D illustrate ellipsometric graphs of the calculated reflected spectrum data corresponding to the three sets of dimension variable values in FIG. 5B.

FIG. 6A is a cross-sectional view illustrating a macro-grating test pattern with a cluster of test pattern lines, an isolated test pattern line, and another cluster of test pattern lines.

FIG. 6B is a table of values of the variable used in a simulation of the reflected spectra from the test pattern in FIG. 6A.

FIG. 6C illustrate reflectometric graphs of the calculated reflected spectrum data corresponding to the three sets of values for the variable width of an isolated test pattern.

DETAILED DESCRIPTION OF PREFERRED EMBODIMENT(S)

Figure 1A:
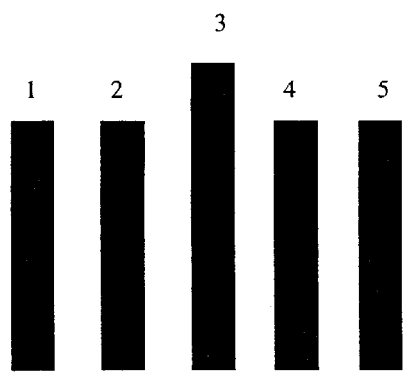
FIG. 1A is cross-sectional view of the prior art five-finger-bar test pattern.

FIG. 1A is cross-sectional view of the prior art five-finger-bar test pattern. Traditional simple test pattern structures in masks like the five-finger-bar test pattern is used to measure the optical proximity effect on profile dimensions. The features or lines are classified according to the density or presence of neighboring lines, e.g., dense lines with many neighboring lines, isolated lines, and in-between lines with some neighboring lines. In FIG. 1A, the middle line 3 may classified as a dense line and the two lines on either side of the middle line, 1, 2, 4, and 5, would be in-between lines.

Figure 1B:
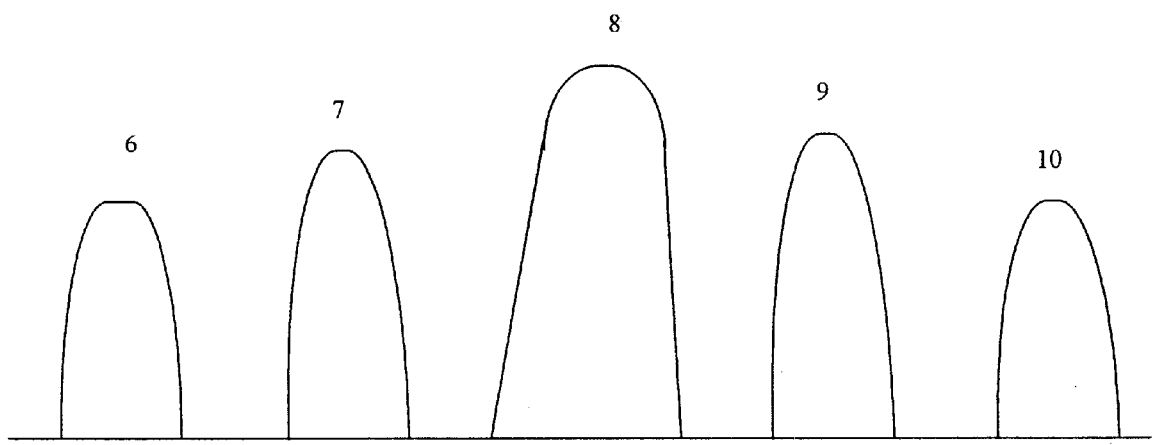
FIG. 1B is a cross-sectional view of the grating feature profile showing the optical proximity effect for the five-finger-bar test pattern.

FIG. 1B is a cross-sectional view of the feature profile showing the optical proximity effect for the five-finger-bar test pattern. Features resulting from the five-finger-bar test pattern mask would have different profiles depending on the proximity and density of other features. For example, the center feature 8 has a bigger height and bottom width than the features at the edge of the test pattern 6 and 10. Optical proximity corrections in the mask and tweaking of other fabrication variables are needed in order to make all the features come closer to the acceptable range of feature dimension.

Figures 2A, 2B:
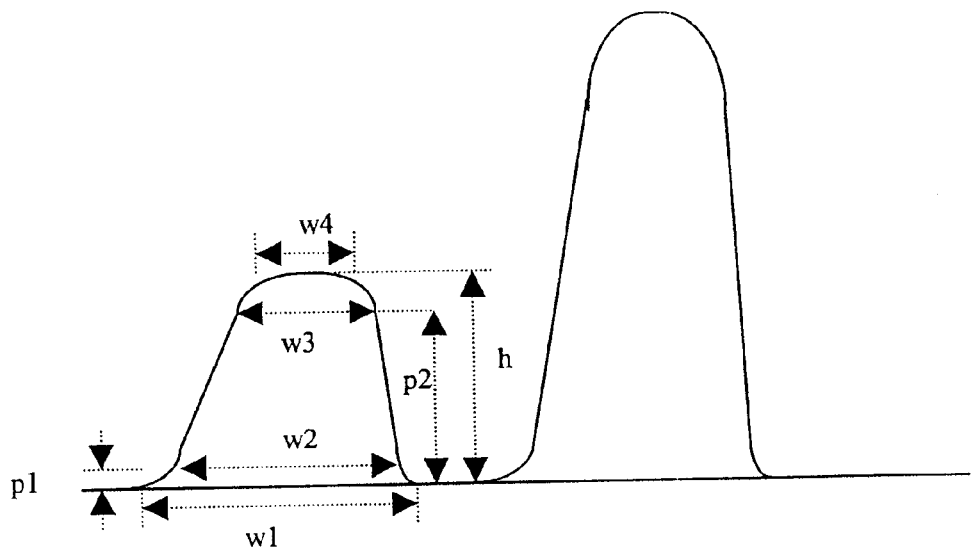
FIG. 2A is a cross-sectional view of a grating profile modeling with a trapezoidal feature profile with top rounding and bottom footing.
FIG. 2B is a table listing the critical dimensions of trapezoidal feature with a top rounding and bottom footing profile.

To model different test pattern profiles, the features are characterized with more dimensions than just the height and width. FIG. 2A is a cross-sectional view of test pattern features with a trapezoidal profile shape that includes top rounding and bottom footing. FIG. 2B is the associated feature dimensions comprising: the feature footing bottom width w1, the trapezoidal bottom width w2, the trapezoidal top width w3, and the rounding top width w4, the bottom foot height p1, the height prior to the top rounding p2, and total height h. Two key dimensional statistics for the trapezoidal feature with top rounding and bottom footing are percent height bottom foot, calculated with the formula: (p1/h)*100; and percent height of top rounding, calculated with the formula: (p2/h)*100.

Some applications may include other profile measurements to account for T-topping, rounding, undercut, concave sidewalls, convex sidewalls, and the underlying thickness whereas other applications use much simpler feature profile dimensions. For the purpose of illustrating the principles of the current invention, only feature top width and distances between neighboring features will be considered in the mathematical models discussed below. However, the principles and concepts of the current invention apply to complex feature profile characterization.

Figure 3:
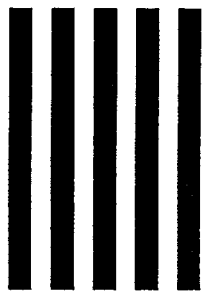
FIG. 3 is a top view of a macro-grating test pattern showing a repeating traditional five-finger-bar test pattern.
Figure 3:
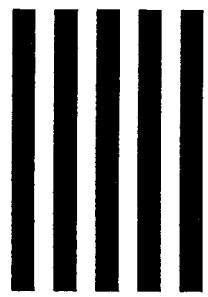
Figure 3:
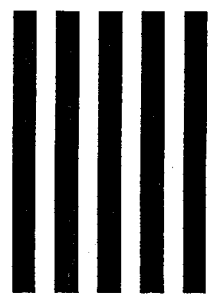

FIG. 3 is a top view of a macro-grating test pattern showing a repeating five-finger-bar test pattern. Macro-grating is the term applied to a test pattern where various combinations of a cluster of test pattern lines and an isolated test pattern line is repeated in a mask. A five-line test pattern 12 is repeated several times as shown in FIG. 3 with two other five-line test patterns 14 and 16. The repetition of the test pattern line set is key to determining the optical proximity effect and the outcome of optical proximity corrections in a test pattern.

Figure 4:
FIG. 4 is a top view of a macro-grating test pattern showing a repeating set of cluster and isolated test pattern lines.
Figure 4:
Figure 4:
Figure 4:
Figure 4:

FIG. 4 is a top view of a macro-grating test pattern showing a repeating set of cluster and isolated test pattern lines. A cluster of three pattern lines 20 separated by some distance from an isolated test pattern line 22 forms a set which is repeated several times as illustrated with another adjacent set consisting of a similar three-line test pattern 24 separated by some distance from an isolated test pattern line 26.

Figure 7:
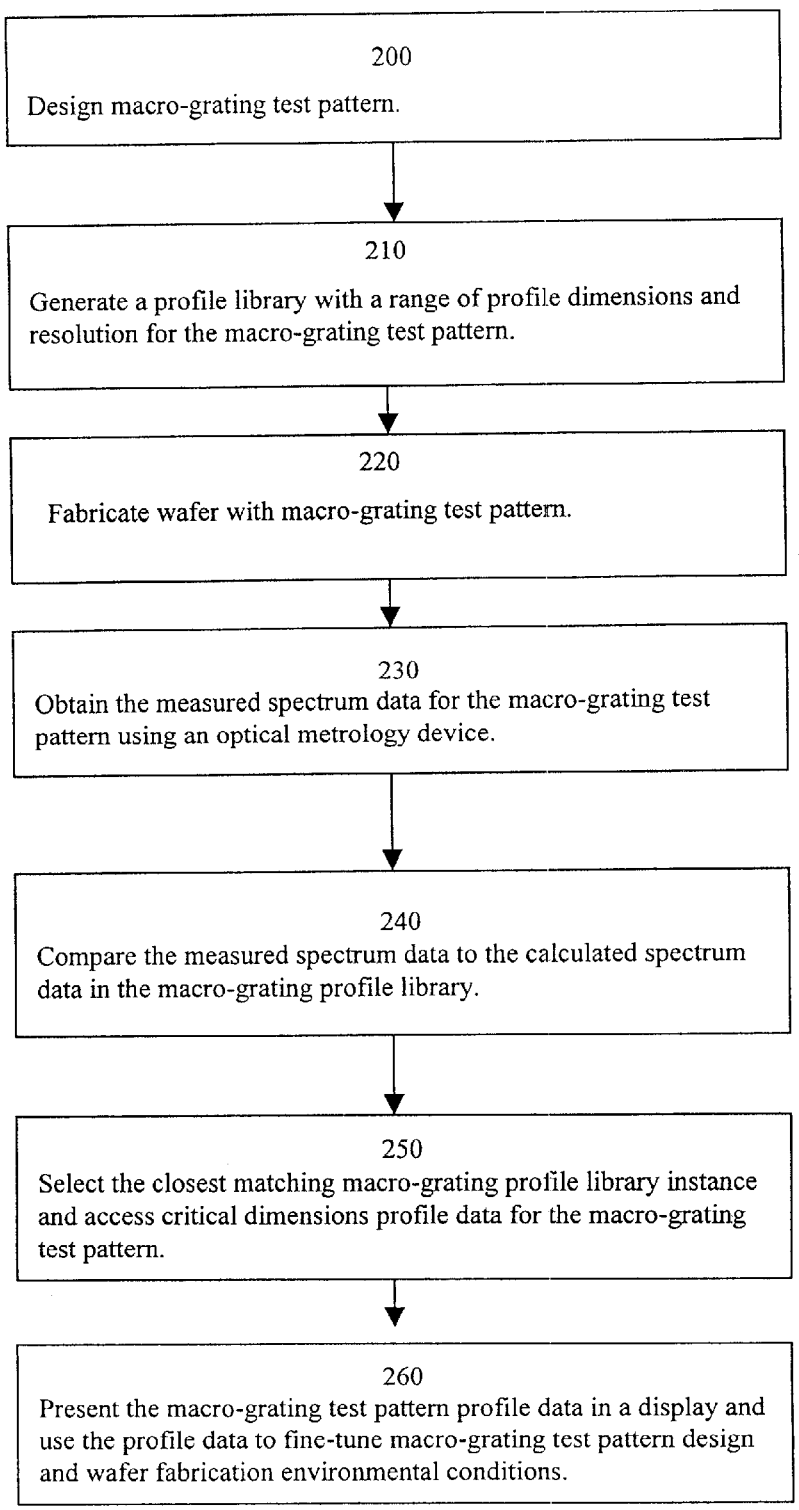
FIG. 7 is flow chart of operational steps of acquiring the macro-grating feature dimensions from the measured spectrum data in one embodiment of the present invention.
Figure 8:
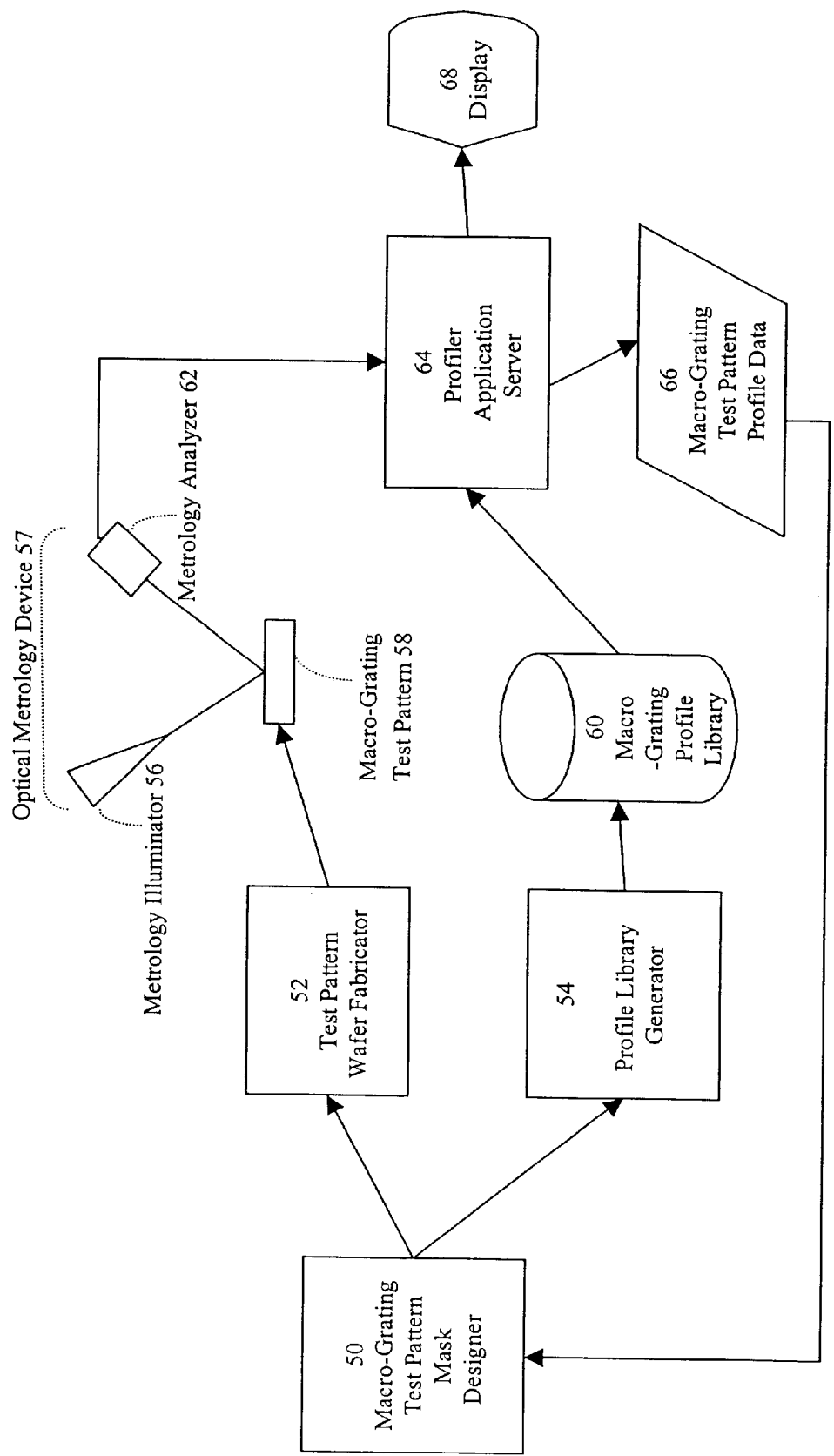
FIG. 8 is an architectural chart of a system for characterizing macro-grating test patterns in one embodiment of the present invention.

One of the objectives of the present invention is a method and a system for getting a more two-dimensional or three-dimensional profile of the grating features of the test pattern in order to evaluate the effect of the use of OPC measures, dummy patterns to compensate for the micro loading effect or the use of phase shift masks. The remaining figures will illustrate the method and the system to use calculated spectrum data to extract the profile dimensions of several configurations of macro-grating test patterns in order to evaluate the effect of corrective measures in designing masks and in grating fabrication processes. The purpose of FIGS. 5A, 5B, and 5C is to illustrate that the profile dimensions of individual features in a macro-grating test pattern can be determined by an ellipsometric metrology device and a spectrum data matching process. FIGS. 6A and 6B illustrate a similar process where the individual features in a different macro-grating test pattern can be determined by a reflectometric device and a similar spectrum data matching process. Ellipsometric, reflectometric or other optical metrology devices may be used. FIGS. 7 and 8 illustrate the method and system where a profile library containing calculated spectrum data is matched against the measured macro-grating test pattern spectrum data to get the macro-grating feature dimensions.

FIG. 5A is a cross-sectional view of a macro-grating test pattern showing a configuration of a cluster of three test pattern lines, a space, followed by another cluster of three test pattern lines. In the first cluster of test pattern lines, the middle test pattern line 32 has a line width represented by the variable L0, the distance between the middle test pattern line 32 and the next pattern line 33 is represented by a variable L1, and the width of the next test pattern line 33 is variable L2. L3 is the variable distance between test pattern line 33 of the first cluster and test pattern line 34 of the second cluster. FIG. 5B is a table of values of the variables used in a calculation of the reflected spectra from the test pattern in FIG. 5A. Three sets of values in nanometers (nm) were selected for the variables L0, L1, L2, and L3 of the macro-grating test pattern in FIG. 5A.

FIGS. 5C and 5D illustrate ellipsometric graphs of the calculated reflected spectrum data corresponding to the three sets of dimension variable values. The X axis in FIG. 5C is the wavelength in nanometers and the Y axis shows tan (Ψ). As can be seen in the graphs in FIG. 5C, the three graphs of tan (Ψ) as a function of the wavelength of the diffracted beam are distinguishable from each other. Since the three graphs are distinguishable from each other, the calculated spectrum data can be matched against the measured spectrum data from the macro-grating test patterns, thereby providing a technique to get profile data of the entire test pattern. FIG. 5D has the wavelength in nanometers in the X axis and the COS (Δ) in the Y axis. Again, as can be seen in the graphs, the three graphs COS (Δ) as a function of the wavelength of the diffracted beam are distinguishable from each other.

FIG. 6A is a cross-sectional view illustrating a macro-grating test pattern with a cluster of test pattern lines, an isolated test pattern line, and another cluster of test pattern lines with the three groups of lines separated by space. In the first cluster of test pattern lines, the middle test pattern line 41 has a constant line width of 150 nm, the distance between the middle test pattern line 41 and the next pattern line 42 is a constant value of 150 nm, the width of the next test pattern line 43 is a constant line width of 150 nm, the distance between the first cluster of test pattern lines and second cluster of test pattern lines is 1,650 nm. L represents the variable width of the isolated test pattern line 43.

FIG. 6B is a table of values for the variable width L of the isolated test pattern line 43. FIG. 6C illustrates reflectometric graphs of the calculated reflected spectrum data corresponding to the three sets of values for the variable width L of the isolated test pattern line 43. The graphs have the wavelength in nanometers in the X axis and the reflectance R in the Y axis. As can be seen in the graphs of FIG. 6C, the three graphs of reflectance R as a function of the wavelength are distinguishable from each other.

FIG. 7 is flow chart of operational steps of characterizing the macro-grating feature dimensions from the measured spectrum data in one embodiment of the present invention. Initially, the design for the macro-grating test pattern is developed 200. The design and placement of the macro-grating test pattern lines depends on the type of grating process effect being measured. Next, a profile library is generated for the macro-grating test patterns 210, based on a set of parameters and the resolution for each parameter. The details of the profile library generation is described in the co-pending U.S. patent application Ser. No. 09-727530, entitled "System and Method for Real-Time Library Generation of Grating Profiles" by Jakatdar, et al., filed on Nov. 28, 2000, owned by the assignee of this application and incorporated herein by reference.

For example, the macro-grating test pattern is similar to the illustration in FIG. 5A, the variables L0, L1, L2, and L3 may be the parameters that can be varied according to the resolution, measured in nanometers, that is desired for the library. The number of parameters selected may include more feature dimensions such as those dimensions listed for a trapezoidal feature with top rounding and bottom footing profile illustrated in FIG. 2B. The major consideration is the length of time and computer resources needed to calculate the spectrum data using the rigorous mathematical model in generating the profile library.

Next, a wafer with the macro-grating test pattern is fabricated 220. The macro-grating test pattern may be fabricated in a reference sample or fabricated in test area separate from the production areas of a wafer. The macro-grating test pattern in the wafer is measured with an optical metrology device to get the spectrum data 230. The spectrum data obtained is compared to the calculated spectrum data in the macro-grating profile library 240 and the closest matching instance in the profile library is selected and the corresponding profile data accessed 250. The profile data comprise dimensions of the features of the macro-grating test pattern lines including the width, height, and other profile dimensions of each feature in the test pattern. For example, if the macro-grating test pattern measured is similar to one illustrated in FIG. 5A, then the profile data obtained in this step would be the values of L0, L1, L2, and L3 in nanometers. If the macro-grating profile library model included the height of the features 32 and 34 as well, then this step would provide the height, in nanometers, of features 32 and 34. As mentioned above, the macro-grating profile library model can include as many critical dimension variables and the process would provide the value of those critical dimension variables from the closest matching profile library instance. The profile data obtained in this step is presented 260 in a display and or stored for later use. In addition, the profile data may be compared with an acceptable range established for the fabrication run and an alert created if the profile data is outside the acceptable range. The same data may also be used to fine-tune the macro-grating test pattern design and or adjust a wafer fabrication environmental condition.

FIG. 8 is an architectural chart of a system for characterizing macro-grating test patterns in one embodiment of the present invention. Initially, the macro-grating test pattern mask designer 50 is used to develop the mask needed to compensate for optical proximity effect, micro-loading effect, or other process effect. The macro-grating mask is used in the test pattern wafer fabricator 52 to produce a wafer containing the macro-grating test pattern. In addition to the test pattern region, the wafer may contain production chips in the product region. In a concurrent process, dimension data associated with the macro-grating test pattern mask is used as parameters to create a profile library using the profile library generator 54. As mentioned above, the process of specifying the parameters and resolution of the parameters for creating the macro-grating profile library 60 is contained in the co-pending U.S. patent application Ser. No. 09/727530, entitled "System and Method for Real-Time Library Generation of Grating Profiles" by Jakatdar, et al., filed on Nov. 28, 2000, owned by the assignee of this application and incorporated herein by reference.

The macro-grating test pattern 58 is measured in an optical metrology device 57 comprising a metrology illuminator 56 projecting the incident beam and a metrology analyzer 62 processing the diffracted beam. The spectrum data obtained by the optical metrology device 57 is transmitted to the profiler application server 64. The profiler application server 64 uses the macro-grating profile library 60 to select the calculated spectrum data that is the "closest match" to the measured spectrum data of the macro-grating test pattern 58 obtained from the optical metrology device 57. The process of obtaining the closest matching instance of the macro-grating profile library 60 using the profiler application server 64 is contained in the co-pending U.S. patent application Ser. No. 09/727530, entitled "System and Method for Real-Time Library Generation of Grating Profiles" by Jakatdar, et al., filed on Nov. 28, 2000, owned by the assignee of this application and incorporated herein by reference. The profile data associated with the closest matching instance of the macro-grating profile library 60 is accessed and stored in a file 66 for immediate or batch processing. The profile data comprising width, height, and other profile dimensions of specific features in the cluster or isolated test pattern line in the macro-grating test pattern may be compared to acceptable ranges established for the fabrication run. An alert is created and displayed in display device 68 if the profile data is outside an acceptable range. The same profile data may also be used to fine-tune the macro-grating test pattern design in the macro-grating test pattern mask designer 50 and or used to adjust a wafer fabrication environmental condition.

Measurement of the macro-grating test pattern with the optical metrology device 57 may be done real-time and the measured spectrum data immediately processed or collected for later batch processing. The process of obtaining profile data 66 for the macro-grating test pattern 58 may be done real-time/in situ with a macro-grating profile library generated previously at the beginning of the fabrication run. The profile data 66 may be used to automatically adjust wafer fabrication environmental factors in an automated wafer fabrication facility.

The benefit of the present invention is that the method and system in non-destructive and can be deployed real-time/in situ to provide profile data on macro-grating test patterns. The present invention also enables the characterization of profile data for all the test pattern lines included in the model to create the profile library. Although relatively straightforward feature dimensions were used in the figures and illustrations, more detailed feature dimensions, such trapezoidal features with top rounding and bottom footing, may be included in the profile library generation step. The principles and method of the present invention would still apply for as long as the calculated spectrum data of a set of test patterns are distinguishable from each other.

In addition to ellipsometers and reflectometers, other optical metrology devices may be used and the principles and methods of the present invention still apply. Examples of other optical metrology devices are single wavelength variable incident angle optical metrology devices, any combination of single wavelength variable incident angle optical metrology devices and multiple wavelength fixed incident angle optical metrology devices, and multiple wavelength multiple incident angle optical metrology devices.

Foregoing described embodiments of the invention are provided as illustrations and descriptions. They are not intended to limit the invention to precise form described. In particular, it is contemplated that functional implementation of invention described herein may be implemented equivalently in hardware, software, firmware, and/or other available functional components or building blocks.

Other variations and embodiments are possible in light of above teachings, and it is thus intended that the scope of invention not be limited by this Detailed Description, but rather by Claims following.

What is claimed is:

1. A non-destructive method for acquiring the profile data of test pattern lines in a macro-grating test pattern the method comprising:

fabricating a set of test patterns in a wafer, wherein the set of test patterns in the wafer is designed to evaluate the effectiveness of corrective measures to compensate for optical proximity or micro-loading effects;

obtain spectrum data from the set of test patterns using an optical metrology device; and accessing the profile data associated with the closest matching calculated spectrum data in a macro-grating profile library.

2. The macro-grating test pattern profile data acquisition method of claim 1, wherein the set of test patterns in the wafer comprises a number of clustered test pattern lines and a number of isolated test pattern lines.

3. The macro-grating test pattern profile data acquisition method of claim 1, wherein the optical metrology device comprises an ellipsometer, a reflectometer, a single wavelength variable incident angle optical metrology device, any combination of a single wavelength variable incident angle optical metrology device and a multiple wavelength fixed incident angle optical metrology device, and a multiple wavelength multiple incident angle optical metrology device.

4. The macro-grating test pattern profile data acquisition method of claim 1, wherein the obtaining of the spectrum data and the accessing the profile data are done real-time at the fabrication line.

5. The macro-grating test pattern profile data acquisition method of claim 1, wherein the profile data comprises width of test pattern lines and distances between test pattern lines.

6. A system for acquiring the profile data of test pattern lines of a macro-grating test pattern comprising:
   a profile library generator for generating a macro-grating profile library comprising profile data and calculated spectrum data;
   an optical metrology device for measuring spectrum data from the macro-grating test pattern;
   a profiler application server for comparing the calculated spectrum data to the measured spectrum data from the optical metrology device;
   wherein the profiler application server selects the closest matching calculated spectrum data in a macro-grating profile library instance, subsequently accessing the associated profile data in the macro-grating profile library instance.

7. The macro-grating test pattern profile data acquisition system of claim 6, wherein the optical metrology device comprises an ellipsometer, a reflectometer, a single wavelength variable incident angle optical metrology device, any combination of a single wavelength variable incident angle optical metrology device and a multiple wavelength fixed incident angle optical metrology device, and a multiple wavelength multiple incident angle optical metrology device.

8. The macro-grating test pattern profile data acquisition system of claim 6, further comprising a macro-grating test pattern mask designer for designing a test pattern comprising a number of clustered test pattern lines and a number of isolated test pattern lines.

9. The macro-grating test pattern profile data acquisition system of claim 6, wherein the profile data associated with the closest matching macro-grating profile library instance comprises width of test pattern lines and distances between test pattern lines.

10. The macro-grating test pattern profile data acquisition system of claim 6, wherein an optical metrology device measuring the spectrum data from the macro-grating test pattern and the profiler application server operate in real-time mode at the fabrication line.

11. The macro-grating test pattern profile data acquisition system of claim 6, wherein the macro-grating test pattern comprises:
   a first cluster of test pattern lines; and
   at least a second cluster of test pattern lines;
      wherein the first and at least second cluster of test pattern lines are separated by a space,
      wherein the test pattern lines of said first and at least second clusters of test pattern, lines are separated by a distance, and
   wherein the space separating the first and at least second cluster of test pattern lines is greater than the distance separating the test pattern lines of said first and at least second clusters of test pattern lies.

12. The macro-grating test pattern profile data acquisition system of claim 6, wherein the macro-grating test pattern comprises;
   a first cluster of test pattern lines, the test pattern lines being separated by a fist distance;
   an isolated test pattern line,
      wherein the first cluster of test pattern lines and the isolated test pattern line are separated by a first spacing, and
      wherein the first spacing is greater than the first distance; and
   a second cluster of test pattern lines, the test pattern lines being separated by a second distance,
      wherein the second cluster of test pattern lines and the isolated test pattern line are separated by a second spacing, and
      wherein the second spacing is greater than the second distance.

13. The macro-grating test pattern profile data acquistion system of claim 12, wherein the first distance and the second distance are equal, and wherein the first spacing and the second spacing are equal.

14. The macro-grating test pattern profile data acquisition method of claim 1, wherein the set of test patterns comprises:
   a first cluster of test pattern lines; and
   at least a second cluster of test pattern lines;
      wherein the first and at least second cluster of test pattern lines are separated by a space,
      wherein the test pattern lines of said first and at least second clusters of test pattern lines are separated by a distance, and
      wherein the space separating the first and at least second cluster of test pattern lines is greater than the distance separating the test pattern lines of said first and at least second clusters of test pattern lines.

15. The macro-grating test pattern profile data acquisition method of claim 1, wherein the set of test patterns comprises:
   a first cluster of test pattern lines, the test pattern lines being separated by a first distance;
   an isolated test pattern line,
      wherein the first cluster of test pattern lines and the isolated test pattern line are separated by a first spacing, and
      wherein the first spacing is greater than the first distance; and
   a second cluster of test pattern lines, the test pattern lines being separated by a second distance,
      wherein the second cluster of test patter lines and the isolated test pattern line are separated by a second spacing, and
      wherein the second spacing is greater than the second distance.

16. The macro-grating test pattern profile data acquisition method of claim 15, wherein the first distance and the second distance are equal, and wherein the first spacing and the second spacing are equal.

17. A method for acquiring the profile data of test pattern lines in a macro-grating test pattern, the method comprising:
   fabricating a set of test patterns configured to indicate optical proximity effects;
   obtaining spectrum data from the set of test patterns using an optical metrology device, and
   accessing the profile data associated with the closest matching calculated spectrum data in a macro-grating profile library.

18. The method of claim 17, wherein the set of test patterns comprises:
   a fat cluster of test pattern lines; and
   at least a second cluster of test pattern lines;
      wherein the first and at least second cluster of test pattern lines are separated by a space,
      wherein the test pattern lines of said first and at least second clusters of test pattern lines are separated by a distance, and wherein the space separating the first and at least second cluster of test pattern lines is greater than the distance separating the test pattern lines of said first and at least second clusters of test pattern lines.

19. The method of claim 17, wherein the set of test pattern comprises:

a first cluster of test pattern lines, the test pattern lines being separated by a first distance;

an isolated test pattern line,
wherein the first cluster of test pattern lines and the isolated test pattern line are separated by a first spacing, and
wherein the first spacing is greater than the first distance; and a second cluster of test pattern lines, the test pattern lines being separated by a second distance,
wherein the second cluster of test pattern lines and the isolated test pattern line are separated by a second spacing, and
wherein the second spacing is greater than the second distance.

20. The method of claim 17, wherein the first distance and the second distance are equals and wherein the first spacing and the second spacing are equal.

* * * * *